(12) United States Patent
Mayer et al.

(10) Patent No.: US 11,096,980 B2
(45) Date of Patent: Aug. 24, 2021

(54) METHOD OF USING GLYCYRRHIZA PLANT-BASED PREPARATION TO REDUCE TOXIC EFFECT OF POLYPEPTIDE FUNGITOXIN

(71) Applicant: Erber Aktiengesellschaft, Getzersdorf bei Traismauer (AT)

(72) Inventors: Elisabeth Mayer, Fels am Wagram (AT); Barbara Novak, Tulln an der Donau (AT); Christina Schwab-Andics, Vienna (AT); Ursula Hofstätter-Schaehs, Vienna (AT); Gerd Schatzmayr, Tulln (AT)

(73) Assignee: ERBER AKTIENGESELLSCHAFT, Getzersdorf bei Traismauer (AT)

( * ) Notice: Subject to any disclaimer, the term of this patent is extended or adjusted under 35 U.S.C. 154(b) by 0 days.

(21) Appl. No.: 16/473,643

(22) PCT Filed: Dec. 14, 2017

(86) PCT No.: PCT/EP2017/001426
§ 371 (c)(1),
(2) Date: Jun. 26, 2019

(87) PCT Pub. No.: WO2018/121881
PCT Pub. Date: Jul. 5, 2018

(65) Prior Publication Data
US 2020/0268819 A1    Aug. 27, 2020

(30) Foreign Application Priority Data
Dec. 28, 2016    (EP) .................................. 16450032

(51) Int. Cl.
*A61K 36/484*    (2006.01)
*A23K 20/163*    (2016.01)
*A23K 10/30*    (2016.01)
*A61K 31/704*    (2006.01)
*A23K 50/30*    (2016.01)
*A23K 50/75*    (2016.01)
*A61K 9/00*    (2006.01)

(52) U.S. Cl.
CPC ............ *A61K 36/484* (2013.01); *A23K 10/30* (2016.05); *A23K 20/163* (2016.05); *A61K 31/704* (2013.01); *A23K 50/30* (2016.05); *A23K 50/75* (2016.05); *A61K 9/0053* (2013.01)

(58) Field of Classification Search
None
See application file for complete search history.

(56) References Cited

U.S. PATENT DOCUMENTS

2014/0005049 A1 *    1/2014    Ilg .......................... A01N 43/82
                                                              504/100

FOREIGN PATENT DOCUMENTS

| CN | 101884421 A | 11/2010 |
| CN | 102872272 A | 1/2013 |
| CN | 103463179 A | 12/2013 |
| CN | 105012673 | * 11/2015 |
| CN | 105012673 A | 11/2015 |
| CN | 105395676 | * 3/2016 |

OTHER PUBLICATIONS

Selvaraj, J. et al. Recent Mycotoxin Survey Data and Advanced Mycotoxin Detection Techniques Reported from China. Food Additives & Contaminants 32(4) 440-452, 2015. (Year: 2015).*
Nasrolahi, A. et al. Survey of Antifungal and Cytotoxic Activity Licorice Extract on Aflatoxin by HPLC Technique. Mycoses 55(Suppl 4) p. 129 #P107, Jun. 2012. (Year: 2012).*
Mohseni R. et al. Antitoxin Characteristic of Licorice Extract. J of Food Safety 34(2)119-125, 2014. (Year: 2014).*
International Search Report, dated Apr. 30, 2018 (3 pages).
R. Mohseni et al., "Antitoxin Characteristic of Licorice Extract: The Inhibitory Effect on Aflatoxin Production in Aspergillus Parasiticus", Journal of Food Safety, vol. 34, No. 2, Jan. 1, 2014, pp. 119-125, cited in the International Search Report.

* cited by examiner

Primary Examiner — Ralph J Gitomer
(74) Attorney, Agent, or Firm — Jacobson Holman PLLC

(57) ABSTRACT

A method of using at least one *Glycyrrhiza* plant preparation selected from the group of flour of a whole, dried *Glycyrrhiza* plant, flour of the leaves of the dried *Glycyrrhiza* plant, flour of roots of the dried *Glycyrrhiza* plant, aqueous dry extract of the *Glycyrrhiza* plant, aqueous/ethanolic dry extract of the *Glycyrrhiza* plant, aqueous extract of the *Glycyrrhiza* plant, optionally together with at least one excipient, for reducing the toxic effect of at least one polypeptide fungitoxin in agrarian products.

7 Claims, No Drawings

METHOD OF USING GLYCYRRHIZA PLANT-BASED PREPARATION TO REDUCE TOXIC EFFECT OF POLYPEPTIDE FUNGITOXIN

BACKGROUND OF THE INVENTION

The present invention relates to the use of at least one *Glycyrrhiza* plant extract, and to an antidote for oral application, for reducing the toxic effect of at least one polypeptide fungitoxin, and the use of said antidote.

*Glycyrrhiza* or licorice plant preparations have been used as remedies since ancient times and are also mentioned in the traditional Chinese medicine as one of the 50 fundamental herbs. *Glycyrrhiza* is a term from Greek already describing the main property of the root of this plant, namely that it tastes sweet and that it is, moreover, the root, "glycos" meaning sweet and "rhize" meaning root. Among all *Glycyrrhiza* species, *Glycyrrhiza glabra* is probably the most relevant one, constituting the most important representative of licorices besides *Glycyrrhiza uralensis*, which is primarily used in the traditional Chinese medicine. The substances contained in the root of licorice inter alia have been known for their anti-inflammatory and mucolytic actions for a long time, a main component among the effectiveness-determining ingredients of the licorice root being, above all, glycyrrhizic acid, in particular 18-beta-glycyrrhizic acid. Glycyrrhizic acid contents vary as a function of the treatment of the licorice root and its origin. Thus, different contents of glycyrrhizic acid can be obtained from one and the same root depending on its treatment. As further important ingredients of the licorice root, about 9% nitrogen-containing substances, up to 3.5% fat, minor contents of tannins, up to more than 30% starch, essential oils, L-asparagine, up to 10% bitterns, and about 4% resins, malic acid and oxalic acid have been identified.

An important component of the licorice root, glycyrrhizic acid, was inter alia investigated by Liu et al. (Zhongguo Zhong Yao Za Zhi, 2014, 39(19), 3841 et seq.) in regard to its effect on lipopolysaccharide-(LPS)-induced cytokine expression in macrophages and found to exhibit anti-inflammatory activity.

Fungitoxins are toxic secondary metabolic products formed by mold fungi. Depending on their type and concentration in feeds, they have negative effects on the performance and health of farm animals in that they may inter alia cause fungitoxin toxicoses. These negative effects include loss of performance, nausea, diarrhea, reduced fertility, weakening of the immune system, the development of cancer, and damage to the nervous system. Fungitoxins thus constitute a health risk, and consequently an economic risk that is at least as large.

It will even be intensified by mold fungi being able to simultaneously form different fungitoxins and secondary metabolites. Therefore, modern analytical methods, which are highly precise, in most cases have detected several fungitoxins and secondary metabolites in raw materials and hence also in feed samples. Streit et al., Toxins, 2013, 5, 504, et seq. found fungitoxins and secondary metabolites in over 90% of the tested raw materials and feed samples. Detected were 7 to 69 metabolites per sample. Due to the presence of synergistic effects not investigated in detail, already very low concentrations of simultaneously occurring fungitoxins may have adverse effects on farm animals.

Different species of mold fungi produce fungitoxins harmful to agriculture, e.g. *Aspergillus, Fusarium* and *Penicillium* (Frisvad et al, Adv. Exp. Med. Biol., 2006, 571, 3, et seq.). The best known and most widely examined mold toxins in the field of animal nutrition include aflatoxins, e.g. aflatoxin B1, trichothecenes, e.g. deoxynivalenol, zearalenone, ochratoxin A and fumonisins, e.g. fumonisin B1.

Document CN10512673A (D1) describes a sweet-wood containing tea product which can be used to inhibit and prevent toxin loads or effects of toxins.

The document RASHIN MOHSENI ET AL: "Antitoxin characteristic of licorice extractr: the inhibitory effect on aflatoxin production in *Aspergillus parasiticus*", JOURNAL OF FOOD SAFETY, WILEY-BLACKWELL PUBLISHING, INC, UNITED STATES, Bd. 34, No. 2, Jan. 1, 2014 (2014-01-01) states that *Glycyrrhiza glabra* extracts have antitoxin activity and are capable of reducing the production of aflatoxins.

By now, more than 500 different fungitoxins and secondary metabolites thereof are known, beauvericin (CAS-No: 26048-05-5), enniatins (CAS-NO: 11113-62-5) such as enniatin A (CAS-No: 2503-13-1), A1 (CAS-No: 4530-21-6), B (CAS-No: 917-13-5), B1 (CAS-No: 19914-20-6), B2, B3 and apicidin (CAS-No: 183506-66-3) being important representatives. In the paper by Streit et al. (Toxins, 2012, 4, 788 et seq.), beauvericin was found in 89%, different enniatins in 96% and apicidin in 66%, of the samples. Enniatins could be detected in 37%, 68% and 76%, respectively, of the tested food samples (n=4.251), feed samples (n=3.640) and in 141 different unprocessed cereal samples (n=2.647), whereas beauvericin was detected in 20%, 21% and 54%, respectively, of the tested food samples (n=732), feed samples (n=861) and 198 different unprocessed cereal samples (n=554). All samples were collected in Europe in the period between 2000 and 2013 (EFSA Journal, 2014, 12, 3802).

Enniatins (ENNs), beauvericin (BEA) and apicidin (API) can be classified in a common group due to their type of synthesis. They are formed by peptide biosynthesis and share a polypeptide structure. Enniatins and beauvericin show symmetric structures and comprise three peptide bonds with alternating ester and amide bonds. Apicidin is not symmetrically structured, comprising four peptide bonds which are amide bonds. In the following, enniatins, beauvericin and apicidin are commonly referred to as "polypeptide fungitoxins" as a subgroup of fungitoxins. The disorders and diseases caused by polypeptide fungitoxins in subjects such as humans and animals are herein referred to as "polypeptide fungitoxin toxicoses". By contrast, deoxynivalenol and aflotoxin B1 are prepared by a completely different path, i.e. by isobutyl biosynthesis, and have a polyisoprene structure.

Polypeptide fungitoxin toxicoses caused by enniatins, beauvericin and apicidin:

Enniatins are known to exhibit cytotoxic effects on mammalian cell lines in in vitro assays. High enniatin contents could be detected in the jejunum, the liver and the fatty tissue of rats, from which it could be concluded that the highest absorption occurs in the jejunum or small intestine. McKee et al. (J. Nat. Prod, 1997, 60, 431 et seq.) demonstrated that high doses of enniatins were lethal to test mice in a study, even low doses having led to losses of weight.

Beauvericin, at least in poultry, is linked with an increase in the heart weight. Already low concentrations of beauvericin cause toxic effects in in vitro assays.

Park et al. (Appl. Environ. Microbiol., 1999, 86, 126 et seq.) showed that apicidin, which is a cyclic histone deacetylase inhibitor, has toxic effects in rats, noticeable by weight loss, bleedings in the abdomen, intestines and bladder, followed by death. Moreover, antiproliferative and cytotoxic effects could be detected in mammalian cell lines.

General signs of polypeptide fungitoxin toxicoses in farm animals, in particular swine and poultry, include lack of appetite and diarrhea, which have negative effects on performance parameters such as live weight, feed conversion ratio, or egg weight.

The first step for avoiding harmful toxins, i.e. both fungitoxins and polypeptide fungitoxins, is the application of suitable agricultural practices and good storage conditions of agrarian products. The analyses of feed samples have, however, demonstrated that these measures are insufficient. Thus, feed additives have been used to protect animals from the adverse effects of fungitoxins on their health and performance. They comprise different ingredients.

Efficient feed additives have already been applied in the event of fungitoxin contaminations of feeds with aflatoxins, zearalenones, trichothecenes, ochratoxin A and fumonisines. However, so far no feed additives acting on the polypeptide fungitoxins: beauvericin, enniatins and/or apicidin have been known.

There is thus a substantial need to reduce the contents of polypeptide fungitoxins in foods and feeds to the largest extent possible, and repress as far as possible any polypeptide fungitoxins contained therein, by the use of feed additives and/or substances or substance groups absorbing or degrading or rendering harmless such polypeptide fungitoxins.

To solve this object, at least one *Glycyrrhiza* plant preparation selected from the group of flour, aqueous extract, aqueous/ethanolic extract, aqueous dry extract and aqueous/ethanolic dry extract of a whole *Glycyrrhiza* plant or of roots of the *Glycyrrhiza* plant, optionally together with at least one excipient for oral use, is used according to the present invention for reducing the toxic effect of at least one polypeptide fungitoxin selected from the group of enniatins, in particular enniatin A, enniatin A1, enniatin B, enniatin B1, enniatin B2 or enniatin B3; beauvericin and apicidin in agrarian products. It has surprisingly been found that when using a *Glycyrrhiza* plant preparation selected from the group of flour, aqueous extract, aqueous/ethanolic extract, aqueous dry extract and aqueous/ethanolic dry extract of a whole *Glycyrrhiza* plant or of roots of the *Glycyrrhiza* plant, it is possible to inhibit the toxic effects of polypeptide fungitoxins selected from the group of enniatins, in particular enniatin A, enniatin A1, enniatin B, enniatin B1, enniatin B2 or enniatin B3; beauvericin and apicidin in agrarian products to such an extent that hazards to a subject consuming the same, in particular humans or animals, no longer exist or, in particular, are substantially reduced.

A nearly complete, in particular substantial, reduction of the toxic effect of at least one polypeptide fungitoxin selected from the group of enniatins, apicidin or beauvericin will be achieved if a *Glycyrrhiza* plant of the group consisting of *Glycyrrhiza glabra* and *Glycyrrhiza uralensis* is used.

When using an aqueous dry extract of the *Glycyrrhiza* plant, in particular from the roots of the *Glycyrrhiza glabra* plant, which contains between 4% (w/w) and 10% (w/w), in particular 7% (w/w), of glycyrrhizic acid, an even further reduction of the effects of specific polypeptide fungitoxins, i.e. beauvericin, enniatins and also apicidin, could surprisingly be achieved, although glycyrrhizic acid itself is known to not show any activity by itself, and the used amount of glycyrrhizic acid is therefore just regarded as an equivalent measure for the active ingredients. By using at least one *Glycyrrhiza* plant preparation according to the present invention, it has become possible to, in particular, completely eliminate the toxic effect of at least one specific polypeptide fungitoxin selected from the group of enniatins, in particular enniatin A, enniatin A1, enniatin B and enniatin B1; beauvericin and apicidin, or reduce the same to such an extent that no harmful effects on the animal or even human organism are to be expected.

The exact dosage of *Glycyrrhiza* plant preparations, and hence the guarantee of a largely complete reduction of the toxic effects of polypeptide fungitoxins, i.e. enniatins, apicidin and beauvericin, will be possible if, as in correspondence with a further development of the invention, the aqueous dry extract, in particular from the roots of the *Glycyrrhiza glabra* plant, with glycyrrhizic acid between 4% (w/w) and 10% (w/w), in particular 7% (w/w), or an equivalent amount of one of the other *Glycyrrhiza* plant preparations according to the present invention, is used in an amount of at least 1 g, preferably from 1 g to 100 g, in a particularly preferred manner from 7 g to 50 g for broilers, in a particularly preferred manner from 5 g to 30 g for laying hens, and in a particularly preferred manner from 5 g to 30 g for pigs, in particular breeding piglets, per ton of agrarian product, in particular feed or food product.

Equivalence refers to the concentrations of the phytogenic materials or substances contained in the *Glycyrrhiza* plant preparations. A well characterized and easily quantifiable substance is glycyrrhizic acid, which is found in the roots of *Glycyrrhiza*. The fraction of glycyrrhizic acid in *Glycyrrhiza* plant preparations serves as an indicator of the concentration of the totality of phytogenic agents or active substances.

By equivalent amount of *Glycyrrhiza* plant preparations, those amounts at which the overall amount of glycyrrhizic acid is equal are understood. Thus, 100 g of a dry extract with 4% (w/w) glycyrrhizic acid is, for instance, equivalent to 50 g of a dry extract with 8% (w/w) glycyrrhizic acid. If, for instance, 50 g of an aqueous dry extract with 10% (w/w) glycyrrhizic acid is used per ton of feed, the administration of 100 g of another *Glycyrrhiza* plant preparation, in particular of another aqueous dry extract, with a content of 5% (w/w) glycyrrhizic acid will be equivalent thereto.

The effectiveness of the *Glycyrrhiza* plant preparations or *Glycyrrhiza* antidotes, or antidotes, according to the invention, in particular their positive effects on the performance parameters of farm animals suffering from polypeptide fungitoxin toxicoses, increases with an increasing amount of *Glycyrrhiza* plant preparations or *Glycyrrhiza* antidotes, or antidotes, used. With polypeptide fungitoxin concentrations in food or feed products of 34 ppb enniatin A, 40 ppb enniatin A1, 510 ppb enniatin B, 392 ppb enniatin B1, 4 ppb enniatin B2, 0.34 ppb enniatin B3, 717 ppb beauvericin and 122 ppb apicidin, clear positive effects on the performance parameters, in particular an increase of the weight and the egg laying rate, and hence a good effectiveness of the *Glycyrrhiza* plant preparations or *Glycyrrhiza* antidotes, or antidotes, against polypeptide fungitoxin toxicoses, are recognizable. The optimum amount of use of the *Glycyrrhiza* plant preparations or *Glycyrrhiza* antidotes, or antidotes, will always correlate with the concentration of polypeptide fungitoxins. The more polypeptide fungitoxins in the food or feed, the larger the required amounts of *Glycyrrhiza* plant preparations or *Glycyrrhiza* antidotes, or antidotes.

Especially good results will be obtained if the *Glycyrrhiza* plant preparations are used such that the agrarian product is selected from foods or feeds consisting of, or containing at least one product contaminated with at least one polypeptide fungitoxin and selected from the group of cereals, corn, rice, soy and other leguminosa, colza, grasses, herbs.

In that, as in correspondence with a further development of the invention, the *Glycyrrhiza* plant preparations are used such that the further contained excipient is selected from the group consisting of inert carriers, vitamins, minerals, phytogenic substances, enzymes and further components for detoxifying mycotoxins, such as mycotoxin-degrading enzymes, in particular aflatoxin oxidases, ergotamine hydrolases, ergotamine amidases, zearalenone esterases, zearalenone lactonases, zearalenone hydrolases, ochratoxin amidases, fumonisin aminotransferases, fumonisin carboxyltransferases, aminopolyol aminoxidases, deoxynivalenol epoxide hydrolases, deoxynivalenol dehydrogenases, deoxynivalenol oxidases, trichothecene dehydrogenases, trichothecene oxidases; and mycotoxin-transforming microorganisms such as DSM 11798; and mycotoxin-binding substances, e.g. microbial cell walls or inorganic materials such as bentonite, it has become possible to also degrade, or render harmless, further polypeptide fungitoxins partially occurring even in major amounts besides the polypeptide fungitoxins: enniatins, beauvericin and apicidin.

In addition to the use of *Glycyrrhiza* plant preparations for reducing the toxic effect of polypeptide fungitoxins in foods or feeds, there has also been the requirement for a product that counteracts the adverse effects of such polypeptide fungitoxins after a possible ingestion of the same.

To solve this object, the present invention further aims at an antidote for oral application for reducing the toxic effect of at least one polypeptide fungitoxin, selected from the group of enniatins, in particular enniatin A, enniatin A1, enniatin B, enniatin 131, enniatin B2 or enniatin B3; beauvericin and apicidin comprising at least one *Glycyrrhiza* plant preparation, selected from the group of flour, aqueous extract, aqueous/ethanolic extract, aqueous dry extract and aqueous/ethanolic dry extract of a whole *Glycyrrhiza* plant or of roots of the *Glycyrrhiza* plant, optionally together with at least one excipient. The oral application of at least one *Glycyrrhiza* plant preparation, optionally together with at least one further excipient, as an antidote enables the neutralization or inhibition or prevention of the adverse effects of polypeptide fungitoxins simultaneously with their ingestion. In that the *Glycyrrhiza* plant preparation is selected from group of flour, aqueous extract, aqueous/ethanolic extract, aqueous dry extract and aqueous/ethanolic dry extract of whole *Glycyrrhiza* plant or of roots of the Glycyrrhia plant it can be ingested together with the possibly contaminated food or feed product so as to immediately prevent any harmful effect on the organism.

A particularly advantageous effect is provided by the antidote if, as in correspondence with a further development of the invention, the *Glycyrrhiza* plant preparation is selected from the group of flour, aqueous extract, aqueous/ethanolic extract, aqueous dry extract and aqueous/ethanolic dry extract of a whole *Glycyrrhiza* plant or of roots of the *Glycyrrhiza* plant, optionally together with at least one excipient. In such a case, it can be ingested together with the possibly contaminated food or feed product so as to immediately prevent any harmful effect on the organism.

The antidote will exhibit an especially advantageous and, in particular, uniformly good activity if the *Glycyrrhiza* plant is selected from the group consisting of *Glycyrrhiza glabra* and *Glycyrrhiza uralensis.*

In that, as in correspondence with a further development of the invention, the aqueous dry extract containing 4% (w/w) to 10% (w/w), in particular 7% (w/w), glycyrrhizic acid is used, the polypeptide fungitoxins contained in food or feed products can be rendered completely harmless upon digestion, wherein the adverse effects of glycyrrhizic acid known from the literature, namely symptoms like hypertension or water retention, will be prevented.

According to a further development of the invention, it is preferably proceeded such that at least 1 g of the aqueous dry extract with a glycyrrhizic acid concentration of 7% (w/w), preferably from 1 g to 100 g, in a particularly preferred manner from 7 g to 50 g for broilers, in a particularly preferred manner from 5 g to 40 g for laying hens, and in a particularly preferred manner from 5 g to 30 g for pigs, in particular breeding piglets, or equivalent amounts are used per ton of agrarian product, in particular feed or food product. It has become possible by such use to almost completely render harmless the polypeptide fungitoxins enniatin, beauvericin and apicidin in food or feed products so as to safely prevent, or even guard against, the occurrence of adverse effects such as symptoms of poisoning in humans and animals.

In that, as in correspondence with a further development of the invention, the antidote is further devised such that it contains more than 50% (w/w), preferably more than 90% (w/w), in particular 100% (w/w), of the at least one *Glycyrrhiza* plant preparation, it has become possible to use the synergistic effects of the ingredients of *Glycyrrhiza* plant preparations. In doing so, it has been surprisingly found that the best-known component of *Glycyrrhiza* plant preparations, i.e. glycyrrhizic acid itself, does not exhibit any activity against polypeptide fungitoxins. The positive action of the *Glycyrrhiza* plant preparations according to the invention against polypeptide fungitoxins is, therefore, based on other ingredients of the licorice root not yet known in detail, or ingredients of the licorice root not known in detail in terms of activity, yet contributing to the desired effect, in particular the prevention of adverse impacts of polypeptide fungitoxins.

In that the antidote is further developed such that the at least one excipient is selected from the group consisting of inert carriers, vitamins, minerals, phytogenic substances, enzymes and further components for detoxifying mycotoxins, such as mycotoxin-degrading enzymes, in particular aflatoxin oxidases, ergotamine hydrolases, ergotamine amidases, zearalenone esterases, zearalenone lactonases, zearalenone hydrolases, ochratoxin amidases, fumonisin aminotransferases, fumonisin carboxyltransferases, aminopolyol aminoxidases, deoxynivalenol epoxide hydrolases, deoxynivalenol dehydrogenases, deoxynivalenol oxidases, trichothecene dehydrogenases, trichothecene oxidases; and mycotoxin-transforming microorganisms such as DSM 11798; and mycotoxin-binding substances, e.g. microbial cell walls or inorganic materials such as bentonite, it has become possible to expand the positive effects to further potentially harmful substances such as mycotoxins from the group of fumonisins, aflatoxins, deoxynivalenol, trichothecenes or ochratoxins.

In this respect, it may preferably be proceeded such that the antidote is used for the production of a preparation for oral use for preventing or treating polypeptide fungitoxin toxicoses. Such a preparation may, in particular, be used for the prophylaxis and treatment of polypeptide fungitoxin toxicoses caused by polypeptide fungitoxins selected from the group of enniatins, in particular enniatin A, enniatin A1, enniatin B, enniatin B1, enniatin B2 or enniatin B3; beauvericin and apicidin. In doing so, it is, in particular, possible to prevent or remedy the harmful effects of polypeptide fungitoxins without involving at the same time any adverse effects caused by glycyrrhizic acid, such as hypertension or the like.

By subjects are to be understood humans and animals, yet in particular farm animals, preferably swine and poultry such as broilers or laying hens, turkeys, cattle or calves.

Polypeptide fungitoxin toxicoses above all can be caused by contaminated feed or food products, i.e. those contaminated with polypeptide fungitoxins, polypeptide fungitoxin amounts of as low as about 500 ppb already showing toxic effects. A polypeptide fungitoxin toxicosis, in particular in livestock, is herein defined as a disease triggered by polypeptide fungitoxins selected from the group of enniatins, in particular enniatin A, enniatin A1, enniatin B, enniatin B1, enniatin B2 or enniatin B3; beauvericin and apicidin and leading to a deterioration of at least one performance parameter by at least 4%, preferably 10%, relative to the positive control group.

With broilers, clear external signs of polypeptide fungitoxin toxicosis, in particular deteriorations of performance parameters, occur at least from a polypeptide fungitoxin overall concentration of about 5000 ppb, in particular 4986.34 ppb.

With laying hens, clear external signs of polypeptide fungitoxin toxicosis, in particular deteriorations of performance parameters, occur at least from a polypeptide fungitoxin overall concentration of about 2000 ppb, in particular 1985 ppb.

In swine, in particular breeding piglets, clear external signs of polypeptide fungitoxin toxicosis, in particular deteriorations of performance parameters, occur at least from a polypeptide fungitoxin overall concentration of about 7000 ppb, in particular 7183.6 ppb.

Any above-described antidote or *Glycyrrhiza* plant preparation may be used as *Glycyrrhiza* antidotes for the treatment and/or prophylaxis of polypeptide fungitoxin toxicoses, an aqueous dry extract from the *Glycyrrhiza glabra* root being preferred.

DESCRIPTION OF THE INVENTION

The effective amount of the *Glycyrrhiza* antidote is a function of the amount of the polypeptide fungitoxins contained in the contaminated feed or food and may also depend on the subject concerned. The effective amount of a *Glycyrrhiza* antidote in the form of a 100% aqueous dry extract from the *Glycyrrhiza glabra* root with a glycyrrhizic acid concentration of 7% (w/w), per kilogram feed or food approximately amounts to:
- at least 1 mg, 1 mg to 100 mg, preferably 7 mg to 50 mg for broilers;
- at least 1 mg, 1 mg to 100 mg, preferably 5 mg to 40 mg for laying hens;
- at least 1 mg, 1 mg to 100 mg, preferably 5 mg to 40 mg for swine, in particular breeding piglets.

It will be clear to the skilled artisan that the 100% aqueous dry extract from the *Glycyrrhiza glabra* root with a glycyrrhizic acid concentration of 7% (w/w) may be replaced with any other herein described *Glycyrrhiza* antidote as soon as the latter is used in an equivalent amount.

This effective amount is sufficient to almost completely render ineffective the toxic activity of polypeptide fungitoxins, thus nearly eliminating the adverse effects of polypeptide fungitoxins on the health of subjects and their performance parameters.

In the following, the invention will be explained in more detail by way of exemplary embodiments.

Example 1: Production of *Glycyrrhiza* Plant Preparations

In the following tests and examples, a spray-dried dry extract containing as end product 7% (w/w) glycyrrhizic acid and 0.003% (w/w) glycyrrhetinic acid was used as *Glycyrrhiza* plant preparation. The contents of glycyrrhizic acid and glycyrrhetinic acid may vary as a function of the starting material and process operation, as known to the skilled artisan. Such *Glycyrrhiza* plant preparations with deviating concentrations of glycyrrhizic acid and glycyrrhetinic acid are also encompassed by the invention, their application amounts having to be adapted to the contents of phytogenic ingredients with a view to ensuring the use of respectively equivalent amounts, based on the content of glycyrrhizic acid.

To produce this extract, it was proceeded as follows: After the harvest of the 3- to 4-year old *Glycyrrhiza glabra* root, the latter was initially disintegrated and triturated with water to a fine pulp, said pulp having been boiled and concentrated for several hours, in particular 3 hours. The extract, after having been filtered and allowed to settle, is further extracted by aqueous vapor extraction under reduced pressure. Thus, a natural, concentrated juice is formed, which is subsequently boiled further under constant stirring and even concentrated further to obtain the aqueous *Glycyrrhiza* extract.

In a further processing and drying step, the aqueous *Glycyrrhiza* extract is spray-dried. This high-speed evaporation technique is based on the drying of small droplets in a tempered, inert drying gas. In doing so, the liquid formulation is atomized into fine droplets and uniformly distributed in the drying air of the spray tower. This leads to an increase in the overall surface area of the liquid and enables the product to be dried within a short time. The end product is a dry, free-flowing powder of relatively uniform particle size, i.e. the *Glycyrrhiza* dry extract. After this, the product is qualitatively assessed and can be redissolved by oral ingestion of subjects, or for carrying out additional tests (Karasaaslaan and Dalgici, J. Food Sci. Technol., 2014, 51(11), 3014 et seq.; Bauer et al., Lehrbuch der Pharmazeutischen Technologie, 2012, ISBN 978-3-8047-2552-2).

Example 2: In Vitro Protective Effect of the *Glycyrrhiza* Dry Extract Against Polypeptide Fungitoxins In order to test the correlations of polypeptide fungitoxins on epithelial tissue under controlled conditions, in vitro studies were performed. Therein, well-characterized test systems based on cell cultures and described in the literature were employed. For feed additives, epithelial cells from the respective organ in question, e.g. in the present case IPEC-J2 cells from the porcine intestine, were preferred. The used epithelial cells from the porcine intestine offer the advantage of being non-transformed cells still having all the important properties of normal intestinal cells and large physiological similarities such as the formation of viable tight junction proteins, which are above all essential for the intestinal barrier, as well as the expression of characteristic enzymes and transport systems (e.g. P-glycoprotein, cytochrome P450 3A4, vit. B 12 transporters etc.).

Such in vitro test systems constitute important and approved methods for predicting in vivo results, even enabling the renunciation of bioavailability studies. A human cell line, Caco-2 cells, which are very similar to IPEC-J2 cells in many aspects, was already published at the end of the 1980s for investigating the transport of pharmaceutical substances. Later on, good correlations between the permeability data obtained from cell monolayers and the oral absorption rate were found. That is why this model found its way into the pharmaceutical industry. Furthermore, the American approval agency, FDA, published a directive on this, providing a context for the so-called Biopharmaceutics Classification System (BCS), the determination of the intestinal permeability by way of validated cell culture systems. Based on such in vitro data, the renouncement of bioavailability studies is possible in certain cases.

For the in vitro examinations of a *Glycyrrhiza* dry extract, the latter was extracted once again, thus producing a secondary *Glycyrrhiza* extract. The secondary *Glycyrrhiza* extract was prepared in that 1 g of the *Glycyrrhiza* dry extract and 9 ml 70% ethanol was each weighed in, mixed, and shaken at 700 rpm for one hour at room temperature. After this, the solution was centrifuged, and the liquid supernatant was sterile filtered using a 0.2 µm filter and further diluted with IPEC-J2 medium. The secondary *Glycyrrhiza* extract was tested in vitro in the following concentrations: 250 µg, 500 µg and 1,000 µg *Glycyrrhiza* dry extract per ml medium in the test formulation, in the following also referred to as 250, 500 and 1,000 µg/ml secondary *Glycyrrhiza* extract.

The fact that ethanolic extracts are able to dissolve more ingredients than do purely aqueous extracts, and thus are closer to the in vivo situation, in which due to the acid or basic conditions and various enzymes in the mouth-gastrointestinal tract also more ingredients are solubilized than by a purely aqueous extraction, was the key reason for secondary extracts with 70% ethanol having been prepared for the in vitro assays.

In the literature, glycyrrhizic acid is considered to be one of the phytogenic main components of the licorice root. The glycyrrhizic acid and glycyrrhetinic acid concentrations in the prepared secondary *Glycyrrhiza* extracts were determined using LC-MS/MS (Agilent 1290 Infinity and Sciex 5500 QTrap). To this end, these extracts were each separated using a Kinetex Biphenyl (100×3 mm) column. Multiple reaction monitoring (MRM) was at 471/105 and 471/119 Da for glycyrrhetinic acid, and 823/453 and 823/647 Da for glycyrrhizic acid. Due to the good solubility of glycyrrhizic acid and glycyrrhetinic acid, it may be anticipated that the total amount contained in the aqueous dry extract is also dissolved in the secondary extract. The prepared *Glycyrrhiza* dry extracts contained 7% (w/w) glycyrrhizic acid and 0.03% (w/w) glycyrrhetinic acid.

The effectiveness of the dosage form in vivo is always a function of the bioavailability of the substance, and hence also of a biokinetic process—this does usually not apply to in vitro experiments. For this reason, higher concentrations have frequently to be used in in vitro experiments in order to be able to observe the same effects as in vivo (Gulden and Seibert, ALTEX 22, Special Issue 2, 2005). The concentrations of 250 µg, 500 µg and 1,000 µg *Glycyrrhiza* dry extract per ml medium, which are used in the present in vitro assays, correspond to in vivo concentrations of about 250 g to 1 kg *Glycyrrhiza* dry extract per ton of feed or food. This is by a factor of 33 to 50 more than the 5 g/t to 30 g/t used in the in vivo tests (cf. Examples 3 to 5).

The TEER technique described by Geens and Niewold (Cytotechnology, 2011, 63, 415 et seq.) was used in an adapted form. In this in vitro model, intestinal porcine epithelial cells (IPEC-J2, DSMZ No.: ACC 701, Passage 1-15) are cultivated in an insert on a permeable polyester membrane (1.12 cm$^2$ surface area, 0.4 µm pore size, 12 mm membrane diameter) and differentiated in the incubator for a period of 8 days at 39° C. and 5% $CO_2$. Per insert, $1\times10^{\wedge 5}$ cells in 0.5 ml medium are applied to the respective membrane. During said differentiation period, the used medium was aspirated every other day and replaced with fresh medium. The insert was fixed in a 12-well cell culture plate, and the cells were supplied with 1.5 ml medium from below (basolateral compartment) and with 0.5 ml medium from above (apical compartment). These compartments reflect the intestinal side (apical "A") and the blood side (basolateral "B"). The medium is a DMEM/Ham's F12 (1:1) medium augmented with 1% IST, 2.5 mM Glutamax, 16 mM Hepes, 6 ng/ml EGF, 5% fetal calf serum and 1001 U/ml penicillin and 100 µg/ml streptomycin.

Differentiated cells form a cell barrier, being strongly interconnected by tight junction proteins. These cells are, moreover, oriented in a polarized manner as in the porcine intestine and can be used as a representative model. Since the intestinal barrier constitutes the first line of defense in the digestive tract against pathogens and toxins, it is important to health that it remains undamaged. The intactness of the cell barrier is measured by means of a volt-ohmmeter: The electrical resistance between the two compartments is referred to as TEER (transepithelial electrical resistance) value and represented in kOhm×cm$^2$. The volt-ohmmeter has to be set to "power" and "R" prior to each measurement. The longer electrode is then introduced into the basolateral compartment, and the shorter electrode is introduced into the apical compartment. In doing so, the cell layer must not be touched.

The secondary *Glycyrrhiza* extract with a concentration of 100 mg/ml is diluted with medium to the desired concentration (250 µg/ml, 500 µg/ml or 1,000 µg/ml). The used medium in the apical compartment is aspirated and supplemented with 250 ml toxin and 250 µl licorice extract (both doubly concentrated in the medium) and incubated for further 72 hours at 39° C. and 5% $CO_2$. After 24 h, 48 h and 72 h, the TEER measurement is performed. All measurements are effected in at least three replicates from which the mean values are taken for further calculations.

TABLE 1

| Time course of TEER cell culture assay | |
|---|---|
| Day 0 | Seeding cells into the inserts |
| Day 2, 4, 7 | Renewing medium |
| Day 8 | Addition of toxins (negativ control); Addition of *Glycyrrhiza* extracts (*Glycyrrhiza* control); No addition (untreated cells; cell control); Addition of toxins and of *Glycyrrhiza* extract; Addition of gycyrrhizic acid |
| Day 9, 10, 11 | TEER value measurement |
| Day 11 | Cytotoxicity test |

The TEER value was constant with the untreated cells (cell control) from day 8 to day 11, likewise after the addition of the secondary *Glycyrrhiza* extract in concentrations of 250 µg/ml, 500 µg/ml or 1,000 µg/ml (*Glycyrrhiza* control) on day 8.

By the addition of the polypeptide fungitoxins, beauvericin, enniatins and apicidin, in different concentrations (0.2-10 µM) (negative control) on day 8, the TEER value was, however, lowered, since the toxins damage the intestinal barrier.

The simultaneous addition of the polypeptide fungitoxins in concentrations of 0.438 µM for apicidin, 5 µM for enniatin A, B, B1, beauvericin, and 10 µM for enniatin A1, each along with the secondary *Glycyrrhiza* extract in concentrations of 250 µg/ml, 500 µg/ml or 1,000 µg/ml showed a significantly smaller or no decrease of the TEER value as compared to the respective negative control. The addition of the secondary *Glycyrrhiza* extract could thus counteract the negative effects of the polypeptide fungitoxins (cf. Table 2). The calculation of the protective effects of the secondary *Glycyrrhiza* extracts relative to the polypeptide fungitoxins was performed according to the following formula:

Protective effect (%)=(TEER mean value (toxin+extract)/TEER mean value (toxin)×100)−100

For instance, for enniatin A [5 µM] incubated with 1,000 µg/ml secondary *Glycyrrhiza* extract, after 24 hours:
TEER mean value enniatin A: 3.928 kOhm×cm$^2$
TEER mean value enniatin A+secondary *Glycyrrhiza* extract: 6.451 kOhm×cm$^2$
Protective effect: (6.451 kOhm×cm$^2$/3.928 kOhm×cm$^2$)× 100)−100=64.2%

Following the last TEER measurement on day 11, a cytotoxicity test (neutral red test) was carried out in order to exclude a cytotoxic effect of the tested toxin and licorice extract concentrations. Tests were exclusively carried out in the non-cytotoxic concentration range with a cell viability of above 99%.

TABLE 2

Protective effect of 250 µg/ml, 500 µg/ml and 1,000 µg/ml secondary *Glycyrrhiza* extract against enniatins A, A1, B, B1, beauvericin and apicidin at three different measurement times (24, 48 and 72 hours, corresponding to days 9, 10 and 11).

| | Toxin | | | | | |
|---|---|---|---|---|---|---|
| Time | ENN A 5 µM | ENN A1 10 µM | ENN B 5 µM | ENN B1 5 µM | BEA 5 µM | API 0.438 µM |
| 250 µg/ml secondary *Glycyrrhiza* extract | | | | | | |
| 24 h | 11.8 | 2.6 | 6.1 | 2.9 | 12.8 | 2.1 |
| 48 h | 34.8 | 11.6 | 4.8 | 3.6 | 2.0 | 3.0 |
| 72 h | 28.5 | 6.8 | 4.6 | 3.5 | 1.5 | 7.7 |
| 500 µg/ml secondary *Glycyrrhiza* extract | | | | | | |
| 24 h | 13.3 | 11.9 | 5.5 | 21.9 | 26.2 | 8.4 |
| 48 h | 36.6 | 23.5 | 8.5 | 16.7 | 18.4 | 16.4 |
| 72 h | 41.4 | 20.3 | 15.0 | 27.3 | 27.6 | 19.6 |
| 1,000 µg/ml secondary *Glycyrrhiza* extract | | | | | | |
| 24 h | 64.2 | 28.9 | 15.3 | 31.4 | 0.3 | 42.4 |
| 48 h | 45.8 | 68.5 | 25.0 | 27.5 | 44.7 | 24.0 |
| 72 h | 37.6 | 72.1 | 21.4 | 59.8 | 19.1 | 17.8 |

The strongest protective effects by the secondary *Glycyrrhiza* extract were to be seen with enniatin A ([1.000 µg/ml] at 24 h and 48 h, [500 µg/ml] at 72 h) and A1 ([1.000 µg/ml] at 48 h and 72 h). With all toxins, a concentration-dependent improvement by secondary *Glycyrrhiza* extracts could be observed. Good effects were also observed against enniatins B and B1, the highest concentration of *Glycyrrhiza* extract (1.000 µg/ml) having, above all, a positive impact on the TEER value. Positive effects against beauvericin and apicidin were observed at 500 µg/ml and 1.000 µg/ml secondary *Glycyrrhiza* extract.

Effect of Glycyrrhizic Acid

In order to investigate a possible effect of glycyrrhizic acid against enniatins A, A1, B, B1, beauvericin and apicidin, glycyrrhizic acid instead of the secondary *Glycyrrhiza* extract was tested at a concentration of 70 µg/ml (corresponding to 1.000 µg/ml secondary *Glycyrrhiza* extract) in the TEER test as described above. Yet, no positive effect could be shown relative to the negative controls. This clearly indicates in a surprising manner that the positive effect of *Glycyrrhiza* plant preparations does not rely on the best-known phytogenic agent of the *Glycyrrhiza* plant, namely glycyrrhizic acid.

Binding Assays

In order to better understand the mechanism of the positive or protective effects of *Glycyrrhiza* plant preparations, binding assays were performed with the aqueous *Glycyrrhiza* dry extract and the polypeptide fungitoxins.

To this end, 1.000 ml buffer solution (1.36 g sodium acetate trihydrate and 0.79 g calcium acetate, pH=8.0) was preincubated with 100 g feed matrix (piglet feed consisting of 50% (w/w) wheat, 10% (w/w) wheat bran, 20% (w/w) soy, 10% (w/w) barley, 10% (w/w) minerals) (24 h at 4° C.) in order to minimize adsorption effects of the hydrophobic toxins on the glass. After this, the solids were centrifuged off, and the clear solution was transferred into 50-ml glass jars each. To such 50 ml, so much aqueous *Glycyrrhiza* dry extract with 7% (w/w) glycyrrhizic acid was each added that the concentration of the extract in the binding assay formulation each amounted to 3 mg/l and 3 g/l, respectively. After this, the toxins, enniatins A, A1, B, B1, beauvericin and apicidin, were added such that the concentrations in the binding assay each amounted to 100 ppb. The binding assay formulations were subsequently incubated at 37° C. under constant stirring for 24 hours. At the beginning and after 24 hours, samples were taken and analyzed for enniatins A, A1, B, B1, beauvericin and apicidin by means of LC-MS/MS as described above. No reduction of the toxin concentration could be measured in any of the tested extract concentrations (3 g/l or 3 mg/l). It is, therefore, excluded that the positive, protective effect of *Glycyrrhiza* plant preparations is brought about by an adsorption or absorption of the toxins on components or by dissolved substances of the *Glycyrrhiza* plant preparation.

Example 3: Feeding Test with Broilers

For assessing the effect of *Glycyrrhiza* plant preparations against polypeptide fungitoxins in poultry, feeding tests with broilers were performed using a *Glycyrrhiza* antidote as feed additive. The *Glycyrrhiza* antidote comprised a 100% aqueous *Glycyrrhiza* dry extract from the roots of the *Glycyrrhiza glabra* plant with a glycyrrhizic acid concentration of 7% (w/w). The aqueous *Glycyrrhiza* dry extract was prepared as described in Example 1.

To this end, 800 Ross broilers having a starting weight of 40 g were assigned to four test groups, each in 10 bays with 20 chicks each. The feed was administered ad lib.

The positive control group received regular chicken feed (phase 1, days 0-14: corn 58%, soy HP 31.25%, premix BR 5%, universal 6.25%, megafat 1.25%, soy oil 2.50%, amino acids 0.50%, monocalcium phosphate 0.25%. Phase 2, days 15-35: corn 6%, soy HP 29.35%, premix BR 5% universal 6.0%, megafat 2.50%, soy oil 2.00%, amino acids 0.15%).

The negative control group received chicken feed of the same formulation as the positive control group, yet contaminated with polypeptide fungitoxins. The overall contamination with polypeptide fungitoxins was 4986.34 ppb, the final chicken feed comprising beauvericin at 1197 ppb, enniatins at 2763.34 ppb (ENN A 34 ppb, ENN A1 175 ppb, ENN B 1700 ppb, ENN B1 803 ppb, ENN B2 51 ppb, ENN B3 0.34) and apicidin at 1026 ppb. The natural contamination by aflatoxin and deoxynivalenol was each <1 ppb and thus negligible.

The two test groups received the same feed contaminated with polypeptide fungitoxins as the negative control group and, in addition, the *Glycyrrhiza* antidote at an admixture rate of 7 g (test group 1) and 50 g (test group 2) per ton of feed. The test period was 35 days, the animals having been weighed on days 0 and 35.

The performance parameters, live weight and feed conversion ratio, are represented in Tables 4 and 5. The animals of the negative control group suffered from polypeptide fungitoxin toxicosis, which caused liquid feces and a significant reduction of the live weight (deterioration by 11.4%) and a deterioration of the feed conversion ratio (deterioration by 4.9%) as compared to the positive control group. The administration of the *Glycyrrhiza* antidote in the two test groups caused a reduction of the toxic effect of the polypeptide fungitoxins, and hence a far less pronounced or no longer present polypeptide fungitoxin toxicosis, thus markedly improving, at both admixture rates, the live weight of the broilers and the feed conversion ratio relative to the negative control group.

The *Glycyrrhiza* antidote or *Glycyrrhiza* plant preparation according to the invention can thus be used for reducing the toxic effect of at least one polypeptide fungitoxin in agrarian products and for increasing the performance parameters, live weight and feed conversion ratio, of feed contaminated with polypeptide fungitoxins for farm animals, in particular broilers, and also for treating and preventing polypeptide fungitoxin toxicoses.

TABLE 4

Effect of the *Glycyrrhiza* antidote or *Glycyrrhiza* plant preparation on the live weight

| Day | Positive control group [g] | Negative control group [g] | Test group 1 [g] | Test group 2 [g] |
|---|---|---|---|---|
| 35 | 1963 | 1739 | 1870 | 1897 |

TABLE 5

Effect of the *Glycyrrhiza* antidote or *Glycyrrhiza* plant preparation on the feed conversion ratio in an observation period of 35 days

| Day | Positive control group [g/g] | Negative control group [g] | Test group 1 [g/g] | Test group 2 [g/g] |
|---|---|---|---|---|
| 1-35 | 1.74 | 1.83 | 1.76 | 1.74 |

Example 4: Feeding Test with Laying Hens

For assessing the effect of *Glycyrrhiza* plant preparations against polypeptide fungitoxins in poultry, feeding tests with laying hens were performed using a *Glycyrrhiza* antidote as feed additive. The *Glycyrrhiza* antidote comprised a 100% aqueous *Glycyrrhiza* dry extract from the roots of the *Glycyrrhiza glabra* plant with a glycyrrhizic acid concentration of 7% (w/w). The aqueous *Glycyrrhiza* dry extract was prepared as described in Example 1.

To this end, 160 Lohmann Brown laying hens were assigned to four test groups, each in 10 bays with 4 hens each. The feed was administered ad lib. The test started at the age of 22 weeks.

The positive control group received regular laying hen feed (wheat 32.1%, corn 30.00%, soy HP 25.00%, calcium carbonate 8.60%, laying hen premix 2.00%, rapeseed oil 1.90%, Biotronic SE forte 0.40%) (Biotronic is a trademark of Erber Aktiengesellschaft).

The negative control group received laying hen feed of the same formulation as the positive control group, yet contaminated with polypeptide fungitoxins. The overall contamination with polypeptide fungitoxins was 1985 ppb, the final laying hen feed comprising beauvericin at 835 ppb, enniatins at 1028 ppb (ENN A 35 ppb, ENN A1 76 ppb, ENN B 510 ppb, ENN B1 392 ppb, ENN B2 15 ppb) and apicidin at 122 ppb. The natural contamination by aflatoxin and deoxynivalenol was each <1 ppb and thus negligible.

The two test groups received the same feed contaminated with polypeptide fungitoxins as the negative control group and, in addition, the *Glycyrrhiza* antidote at an admixture rate of 5 g (test group 1) and 40 g (test group 2) per ton of feed. The test period was 14 days.

The performance parameters, egg-laying rate (percentage of hens laying an egg per day), average egg weight and feed conversion ratio, were determined during the test period and are represented in Table 6. The animals of the negative control group suffered from polypeptide fungitoxin toxicosis, which caused liquid feces and, in particular, a significant deterioration of the performance parameters (egg-laying rate: deterioration by 6.1%; egg weight: deterioration by 3.6%; feed conversion ratio: deterioration by 7.1%). The administration of the *Glycyrrhiza* antidote in the two test groups caused a reduction of the toxic effect of the polypeptide fungitoxins, and hence a far less pronounced or no longer present polypeptide fungitoxin toxicosis, thus markedly improving, at both admixture rates, the performance parameters relative to the negative control group.

The *Glycyrrhiza* antidote or *Glycyrrhiza* plant preparation according to the invention can thus be used for reducing the toxic effect of at least one polypeptide fungitoxin in agrarian products and also for increasing the performance parameters, egg-laying rate, average egg weight and feed conversion ratio, of feed contaminated with polypeptide fungitoxins for farm animals, in particular laying hens, and also for treating and preventing polypeptide fungitoxin toxicoses.

TABLE 6

Performance parameters

| | Positive control group | Negative control group | Test group 1 | Test group 2 |
|---|---|---|---|---|
| Egg-laying rate [%] | 99 | 93 | 96 | 98 |
| Average egg weight [g] | 56 | 54 | 55 | 56 |
| Feed conversion ratio [g/g] | 1.83 | 1.97 | 1.89 | 1.84 |

Example 5: Feeding Test with Breeding Piglets

For assessing the effect of *Glycyrrhiza* plant preparations against polypeptide fungitoxins in pigs, a feeding test with breeding piglets was performed using a *Glycyrrhiza* antidote as feed additive. The *Glycyrrhiza* antidote comprised a 100% aqueous *Glycyrrhiza* dry extract from the roots of the *Glycyrrhiza glabra* plant with a glycyrrhizic acid concentration of 7% (w/w). The aqueous *Glycyrrhiza* dry extract was prepared as described in Example 1.

To this end, 120 breeding piglets were assigned to four test groups, each in 10 pens with 3 piglets each. The feed was administered ad lib. The test started with 4-week-old piglets weighing 7.7 kg.

The positive control group received regular breeding piglet feed (phase 1, days 1-14: corn 32.00%, barley 34.90%, protein premix 23%, sunflower oil 1.00%, dextrose 4.00%, lactose 3.00%, piglet premix 2.1%. Phase 2, days 15-56: corn 41.00%, barley 35.00%, soy HP 20.00%, sunflower oil 0.50%, piglet premix 3.5%).

The negative control group received breeding piglet feed of the same formulation as the positive control group, yet contaminated with polypeptide fungitoxins. The overall contamination with polypeptide fungitoxins was 7183.6 ppb, the final breeding piglet feed comprising beauvericin at 717 ppb, enniatins at 4733.6 ppb (ENN A 86 ppb, ENN A1 40 ppb, ENN B 1492 ppb, ENN B1 3111 ppb, ENN B2 4 ppb, ENN B3 0.6 ppb) and apicidin at 1733 ppb. The natural contamination by aflatoxin and deoxynivalenol was each <1 ppb and thus negligible.

The two test groups received the same feed contaminated with polypeptide fungitoxins as the negative control group and, in addition, the *Glycyrrhiza* antidote at an admixture rate of 5 g (test group 1) and 30 g (test group 2) per ton of feed. The test period was 56 days.

The performance parameters, live weight and feed conversion ratio, were determined at the end of the test period and are represented in Table 7. The animals of the negative control groups suffered from polypeptide fungitoxin toxicosis, which caused lack of appetite, diarrhea and, in particular, a significant deterioration of the performance parameters (live weight: deterioration by 17.1%; feed conversion ratio: deterioration by 6.4%). The administration of the *Glycyrrhiza* antidote in the two test groups caused a reduction of the toxic effect of polypeptide fungitoxins, and hence a far less pronounced or no longer present polypeptide fungitoxin toxicosis, thus markedly improving, at both admixture rates, the performance parameters relative to the negative control group.

The *Glycyrrhiza* antidote or *Glycyrrhiza* plant preparation according to the invention can thus be used both for reducing the toxic effect of at least one polypeptide fungitoxin in agrarian products and for increasing the performance parameters, live weight and feed conversion ratio, of feed contaminated with polypeptide fungitoxins for farm animals, in particular swine, and also for treating and preventing polypeptide fungitoxin toxicoses.

TABLE 7

Performance parameters

| | Positive control group [kg] | Negative control group [kg] | Test group 1 [kg] | Test group 2 [kg] |
|---|---|---|---|---|
| Average live weight day 56 | 35 | 29 | 32 | 33 |
| Feed conversion ratio [kg/kg] | 1.59 | 1.70 | 1.65 | 1.62 |

The invention claimed is:

1. A method for reducing toxic effect of at least one polypeptide fungitoxin selected from the group of enniatin A, enniatin A1, enniatin B, enniatin B1, enniatin B2, enniatin B3, beauvericin and apicidin in agrarian products, the method comprising the step of orally administering to a subject at least one *Glycyrrhiza* plant preparation selected from the group of flour, aqueous extract, aqueous/ethanolic extract, aqueous dry extract and aqueous/ethanolic dry extract of a whole *Glycyrrhiza* plant or of roots of the *Glycyrrhiza* plant, together with at least one excipient for oral administration.

2. The method according to claim 1, wherein the *Glycyrrhiza* plant is selected from the group consisting of *Glycyrrhiza glabra* and *Glycyrrhiza uralensis*.

3. The method according to claim 1, wherein the aqueous dry extract comprises glycyrrhizic acid at a concentration of 4% (w/w).

4. The method according to claim 1, wherein the aqueous dry extract is used in amount of 1 g to 100 g per ton of agrarian product, or an equivalent amount of one of the *Glycyrrhiza* plant preparations selected from the group of flour, aqueous extract, aqueous/ethanolic extract and aqueous/ethanolic dry extract of a whole *Glycyrrhiza* plant or of roots of the *Glycyrrhiza* plant, per ton of agrarian product.

5. The method according to claim 1, wherein the toxic effect of at least one polypeptide fungitoxin is completely eliminated.

6. The method according to claim 1, wherein the agrarian product is selected from foods or feeds consisting of, or containing, at least one product selected from the group of cereals, corn, rice, soy and other leguminosa, colza, grasses, herbs.

7. The method according to claim 1, wherein the excipient is selected from the group consisting of inert carriers, vitamins, minerals, phytogenic substances, enzymes and further components for detoxifying mycotoxins, namely mycotoxin-degrading enzymes, aflatoxin oxidases, ergotamine hydrolases, ergotamine amidases, zearalenone esterases, zearalenone lactonases, zearalenone hydrolases, ochratoxin amidases, fumonisin aminotransferases, fumonisin carboxyltransferases, aminopolyol aminoxidases, deoxynivalenol epoxide hydrolases, deoxynivalenol dehydrogenases, deoxynivalenol oxidases, trichothecene dehydrogenases, trichothecene oxidases; and mycotoxin-transforming microorganisms DSM 11798; and mycotoxin-binding substances, selected from microbial cell walls or bentonite.

* * * * *